United States Patent [19]

Nesbitt

[11] Patent Number: 4,620,535

[45] Date of Patent: Nov. 4, 1986

[54] IMMOBILIZER FOR A PATIENT

[76] Inventor: William R. Nesbitt, 6967 Blue Oak La., Loomis, Calif. 95650

[21] Appl. No.: 645,243

[22] Filed: Aug. 29, 1984

[51] Int. Cl.$^4$ ............................................. A61F 13/00
[52] U.S. Cl. .................................... 128/134; 269/328
[58] Field of Search ................. 128/134, 133, 94, 78, 128/DIG. 15; 269/328, 322; 119/96; 70/16, 18; 248/499

[56] References Cited

U.S. PATENT DOCUMENTS

| 3,256,880 | 6/1966 | Caypinar | 128/133 |
| 3,297,026 | 1/1967 | Van Pelt | 128/133 |
| 3,358,141 | 12/1967 | Hoffmann et al. | 128/134 X |
| 3,526,222 | 9/1970 | Dreibelbis | 128/134 |
| 3,650,523 | 3/1972 | Darby, Jr. | 128/134 X |
| 3,829,079 | 8/1974 | Fox | 269/328 |
| 4,010,744 | 3/1977 | Boyen | 128/75 |
| 4,046,143 | 9/1977 | Bell | 128/133 |
| 4,091,808 | 5/1978 | Nelson | 128/133 |
| 4,127,120 | 11/1978 | Applegate | 128/134 |
| 4,223,670 | 9/1980 | Cramer | 128/134 |

FOREIGN PATENT DOCUMENTS 145434  2/1951  Australia ............... 128/134

Primary Examiner—Mickey Yu
Attorney, Agent, or Firm—Lothrop & West

[57] ABSTRACT

For use in immobilizing an infant, particularly, or an adult patient, there is provided a stiff anchor plate having apertures therethrough arranged to define bars engageable by straps passing through the apertures and releasably connected at various points to establish loops of various lengths to engage the patient's ankles and wrists and to lie behind and partially around his neck to hold him in approximately a fetal position.

4 Claims, 4 Drawing Figures

IMMOBILIZER FOR A PATIENT

CROSS-REFERENCES TO RELATED APPLICATIONS

My design patent application for the appearance of a related structure was filed Jan. 16, 1984 with U.S. Ser. No. 571,031.

BRIEF SUMMARY OF THE INVENTION

An immobilizer for a patient is for use in holding a patient in a particular position to preclude his undue movement while undergoing medical examination or treatment. The structure is adapted for use with infants, particularly to hold them in an approximately fetal position, and also with adults.

PRIOR ART AND INFORMATION DISCLOSURE

A preliminary search has yielded the following patents:

U.S. Pat. No. 3,297,026, Jan. 10, 1967, Van Pelt
U.S. Pat. No. 3,526,222, Sept. 1, 1970, Dreibelbis
U.S. Pat. No. 3,829,079, Aug. 13, 1974, Fox
U.S. Pat. No. 4,010,744, Mar. 8, 1977, Boyen
U.S. Pat. No. 4,046,143, Sept. 6, 1977, Bell
U.S. Pat. No. 4,091,808, May 30, 1978, Nelson A copy of each patent listed is attached.

The Van Pelt patent device is not self-contained, but requires an external, separate fastening support.

The Dreibelbis patent structure is not usable to produce a fetal position.

The Fox patent structure produces a fetal position but without substantial restraint of the patient's arms or legs.

The Boyen patent device interconnects shoulder-chest straps and heel straps but does not restrain the arms nor produce a fetal position.

The Bell patent discloses a bar with leg cuffs to prevent the patient crossing his legs but does not produce a fetal position.

The Nelson patent structure immobilizes one leg in a flexed position but does not restrain the upper body nor the arms.

DETAILED DESCRIPTION

Figure 2:
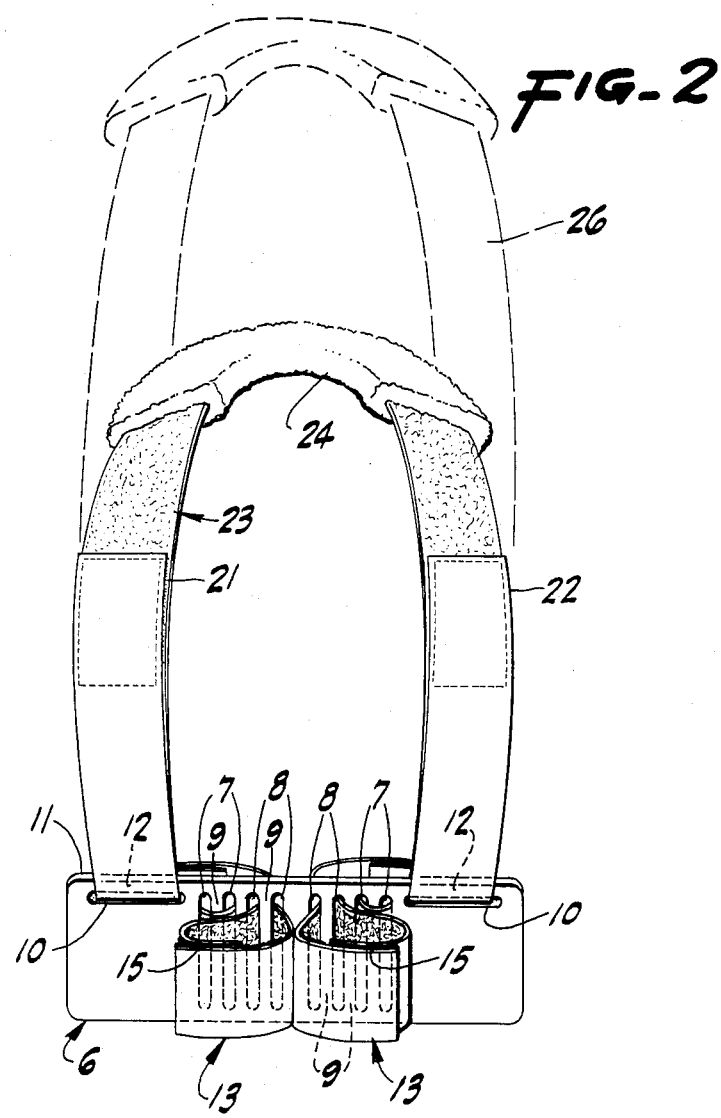
FIG. 2 is a perspective view from the front showing the immobilizer separate from a patient and in location to establish a fetal position.
Figure 3:
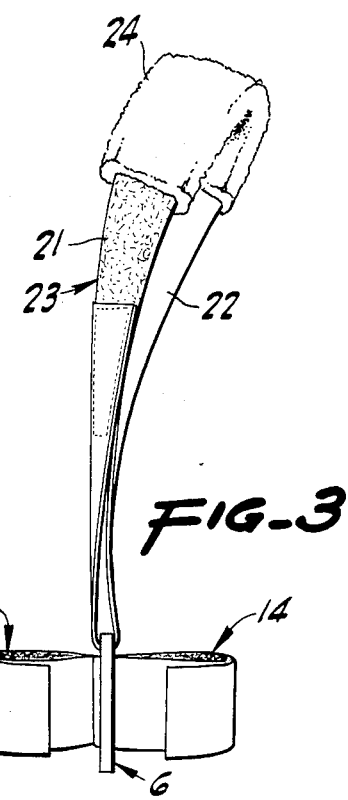
FIG. 3 is a side elevation of the structure of FIG. 2.
Figure 4:
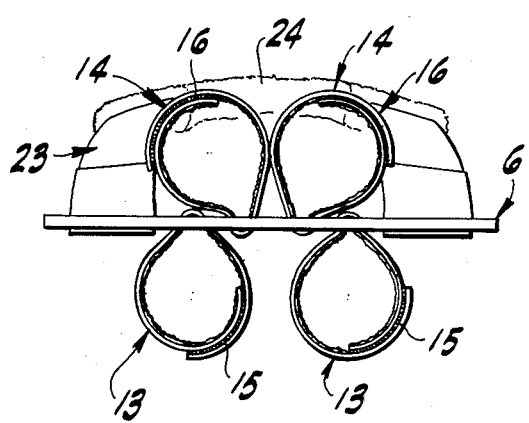
FIG. 4 is a plan of the structure shown in FIG. 2.
Figure 1:
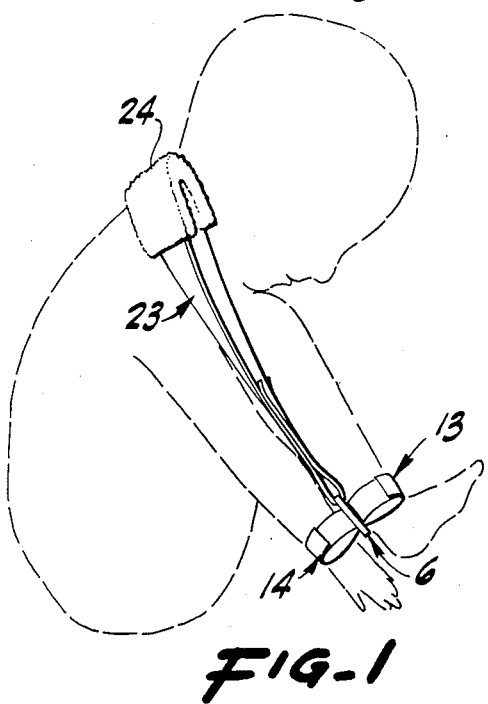
FIG. 1 is a side elevation of the immobilizer of the invention as applied to hold an infant in a substantially fetal position.

There are many instances in which it is necessary to restrain an individual, particularly an infant, although the disclosed device is not limited to infant use, in order to give him an examination or medical treatment. To do this there has been provided an anchor plate 6. This is a relatively stiff member not readily distorted in use. The anchor plate is generally rectangular in aspect and is elongated to extend substantially transversely of or across the patient when used on him. The anchor plate has gently rounded corners and edges in order to avoid any injury to the patient. The plate is provided with a number of pairs of apertures 7 and 8, for example, which extend transversely of the plate and provide between each pair of apertures an intervening, rounded bar 9.

Another pair of apertures 10 preferably extends longitudinally of the plate and together with the parallel, adjacent, longitudinal edge 11 of the plate define longitudinally extending, rounded bars 12 near the ends of the plate.

Adapted to extend through adjacent pairs of the apertures 7 and 8 are pairs of straps 13 and 14 located by the apertures and bars 9 on the base plate in positions adapted to be easily engageable with the ankles and wrists of the patient. Each of the straps, except for length, is like the others. Each strap is preferably made of quite flexible, relatively strong, soft woven fabric. There is a fastening means 15 on a strap, adjacent one end thereof, adapted to interengage with a complimentary fastening means 16 near the other end of the same strap. The fastening engagement can be of the "Velcro" type and is effective when secured in various different locations to vary the length of the secured strap and to permit separation, when desired, of the strap ends by means of a manual release. The similar set of pairs of straps are arranged for engagement with the patient's wrists and ankles to hold them close together, usually but not necessarily on opposite sides of the anchor plate 6.

Two portions of a neck strap 23 pass through the pair of apertures 10 and are detachably secured together. The ends of the strap 23 are detachably secured together by fastening means 21 and 22 similar to means 15 and 16 described above. The neck strap 23 has its flat, looped portions generally lying in the same plane as the plate 6 although the intermediate portion of the strap, when the ends are fastened together, is adapted to conform to the contour of the back of the patient's neck. The straps 13 and 14 generally extend with their flat portions perpendicular to the surface of the plate 6.

Conveniently, the neck portion of the strap 23 is covered by a protective shield 24 of relatively soft material put upon or fastened around the strap 23.

In the use of this device, the anchor plate 6 is placed near (ahead of or behind) the legs of the patient. The pairs of straps 13 are placed around his ankles and are fastened with a moderately tight interengagement, so that the patient's legs cannot move materially with respect to the stiff anchor plate. Similarly, the pairs of straps 14 are wrapped around the wrists of the patient and fastened after his wrists have been brought into close proximity to his ankles. The wrists and arms and the ankles and legs are then not substantially movable with respect to the plate 6 nor with respect to each other.

Finally, the neck strap 23 is placed against the back of the patient's neck when his head and spine have been positioned in a curve to approximate a fetal position. The strap ends are then fastened together. Under these circumstances, the patient presents a bowed or convex spine readily available for treatment or diagnosis. The treatment is relatively short and the straps are removed quickly by an inverse operation separating the fasteners from each other. When the device is separated from the patient it can be folded compactly and retained for sterilization and for future use on another patient.

Although the device is primarily designed for infant use, it is possible by providing longer straps, such as shown by the dotted line strap 26 in FIG. 2, to utilize a similar technique for holding an adult in a similar substantially fetal position.

With infants and very young children, it may not be necessary to use the wrist engaging straps for the patient is not advanced enough to endeavor to release any of the strap fasteners. Consequently, his hands and arms may be left free. Yet, for older patients it is most often advisable to use the leg and arm restrictions together.

If desired, legends (not shown) can be placed on the individual straps near the anchor plate to indicate the limb to which the particular loop is to be applied and also to indicate whether the loop is to be used and tightened in front of or in back of the anchor plate.

I claim:

1. An immobilizing restraint device for use in connection with a lumbar puncture procedure wherein it is necessary to temporarily maintain a patient in a substantially fetal position comprising:
   (1) an anchor plate including a generally rigid rectangular body portion;
   (2) means defining a first plurality of slotted openings extending through said body portion in generally parallel relation with the short sides of said rectangular body;
   (3) means defining a second plurality of slotted openings extending through said body portion in generally parallel relation to the long sides of said rectangular body and generally perpendicular to said first plurality of slotted openings;
   (4) a pair of adjustable wrist encircling retention straps entrained through selected ones of said first plurality of slotted openings and configured to encircle and restrain the patient's wrists in close proximity to each other and to said anchor plate;
   (5) a pair of adjustable ankle encircling retention straps entrained through selected other ones of said first plurality of slotted openings and configured to encircle and restrain the patient's ankles in close proximity to each other and to said patient's wrists; and
   (6) a neck retention strap entrained through said second plurality of openings extending through said body portion and configured to extend around the back of the patient's neck and adjustably maintain the patient's upper body in a position with respect to the patient's arms and legs in a generally fetal position with the spinal column in a generally arched configuration.

2. A device as in claim 1 in which the leg retention straps extend away from one side of said anchor plate and are spaced apart a distance corresponding to the spacing between the ankles of a patient.

3. A device as in claim 1 in which the wrist retention straps extend away from the opposite side of said anchor plate from said leg retention straps and are spaced apart a distance corresponding to the spacing between the wrists of a patient.

4. A device as in claim 1 in which said anchor plate is substantially inflexible under loads placed thereon by said straps.

* * * * *